United States Patent [19]

Kaufhold et al.

[11] Patent Number: 4,722,808
[45] Date of Patent: Feb. 2, 1988

[54] USE OF CYCLODODECENYLACETONITRILE AS A FRAGRANCE COMPONENT

[75] Inventors: Manfred Kaufhold, Marl, Fed. Rep. of Germany; Slagmulder Andre, Beauchamp, France

[73] Assignee: Huels Aktiengesellschaft, Marl, Fed. Rep. of Germany

[21] Appl. No.: 857,221

[22] Filed: Apr. 29, 1986

Related U.S. Application Data

[62] Division of Ser. No. 690,223, Jan. 10, 1985.

[30] Foreign Application Priority Data

Jan. 11, 1984 [DE] Fed. Rep. of Germany ....... 3400689

[51] Int. Cl.$^4$ .............................................. A61K 7/46
[52] U.S. Cl. ........................................ 512/6; 252/132; 252/174.11; 558/303; 558/371; 558/378; 558/435
[58] Field of Search .................................... 252/522 R

[56] References Cited

U.S. PATENT DOCUMENTS 4,579,680 4/1986 Sell ................................. 252/522 R Primary Examiner—Howard T. Mars
Assistant Examiner—Vera C. Clarke
Attorney, Agent, or Firm—Millen & White

[57] ABSTRACT

Cyclododecenylacetonitrile is prepared by reacting cyclododecanone with cyanoacetic acid in the presence of a catalyst. Purified cyclododecenylacetonitrile has a pleasant scent reminiscent of roses and lilies of the valley, containing additionally a musk note, and is suitable as a fragrance and as a fragrance component.

10 Claims, No Drawings

USE OF CYCLODODECENYLACETONITRILE AS A FRAGRANCE COMPONENT

This is a division of application Ser. No. 690,223 filed Jan. 10, 1985.

BACKGROUND OF THE INVENTION

This invention relates to the use of cyclododecenylacetonitrile as a fragrance or in fragrance compositions.

Cyclododecenylacetonitrile has been prepared by the condensation of cyclododecanone with acetonitrile in the presence of strongly alkaline catalysts, Stephen A. DiBiase et al., Journal of Org. Chem. 44, No. 25, page 4640, (1979). A mixture of the isomers (1) and (2), in cis and trans form, is obtained in an overall yield of about only 45%.

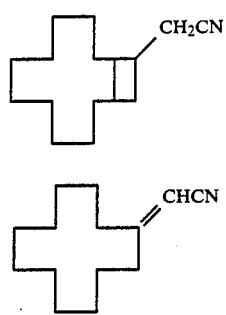

Such a low yield inhibits commercial exploitation of the product.

OBJECT OF THE INVENTION

An object of the present invention is to provide a fragrance composition containing cyclododecenylacetonitrile.

Upon further study of the specification and appended claims, further objects and advantages of this invention will become apparent to those skilled in the art.

SUMMARY OF THE INVENTION

Cyclododecenylacetonitrile, as a mixture of its cis and trans isomers, is obtained in an overall yield of more than 70% by the Knoevenagel reaction of cyclododecanone with cyanoacetic acid in the presence of a conventional Knoevenagel catalyst, such as ammonia or an amine, for example piperidine, β-alanine etc., preferably also in the presence of a carboxylic acid, for example, glacial acetic acid. Ammonium acetate is a preferred catalyst for the reaction because it is readily separable from the products of the reaction, it has the advantage of being very inexpensive, and does need not be recovered.

Organic chemistry textbooks state that good yields of product are obtained in the Knoevenagel reaction when short-chain ketones or carbonyl compounds activated by an aromatic ring are employed. In the aliphatic ketones series, e.g., acetone, butanone and cyclohexanone, the yields of product drop from 90% to 70%. In other words, the yield declines significantly as the chain length or number of carbon atoms increases, Organikum, 12th ed., VEB Deutscher Verlag der Wissenschaften, Berlin, 1973, page 508.

Thus, it could not be expected that the Knoevenagel reaction in a complex ring system having twice as many carbon atoms as cyclohexanone would give good yields of product. Nor could it be forseen that a ketone with 12 carbon atoms gives with cyanoacetic acid in the presence of a very weak alkaline catalyst (in contrast to the method described by Stephen A. DiBiase et al.) a more than 70% yield of the correspondingly substituted acetonitrile.

In practicing the process of the present invention, cyclododecanone is reacted with cyanoacetic acid in a molar ratio of 5:1 to 1:5, preferably 1:2 to 1:1, in the presence of 5-1% by weight, preferably 3-2% by weight of a conventional Knoevenagel catalyst based on cyclodedecanone, at 100°-170° C. and preferably 120°-140° C. The reaction product is purified by distillation under vacuum, typically at 1-50 mbar. Cyclododecenylacetonitrile, containing a small quantity of (2), is obtained in a purity of above 99% but has an odor resembling ammonia. After pasing an inert gas, such as, for example, nitrogen, e.g., 50-200 liters of nitrogen, through 1-5 liters of the mixture of cyclododecenylacetonitrile isomers for a period of 0.5-5 hours, preferably 1-3 hours, at 10°-100° C., and preferably 15°-30° C., the ammonia odor completely disappears.

Following treatment with and inert gas, the cyclododecenylacetonitrile as an unexpected, pleasant fragrance reminiscent of roses and lilies of the valley and additionally comprising a musk note. Cyclododecenylacetonitrile (1) and its isomer (2), as well as their mixture, exhibit superior fragrance quality and also exhibit unexpectedly good properties as fragrance components. There has been no suggestion heretofore that these comounds, in the pure form, have a good fragrance quality.

There exists great interest in fragrances that can be readily and economically manufactured, show great chemical stability, and possess a broad spectrum of usage possibilities in various fragrance compositions. These properties are displayed by nitriles (1) and (2), and by their mixture to a surprisingly high degree. In comparison with many other fragrances, such as, for example, esters and aldehydes, cyclododecenylacetonitrile resists chemical attack and is stable in a pH range of about 3-14. On account of its unexpectedly high resistance to alkali, it is particularly suitable for the perfuming of detergents, soaps, etc.

Compounds (1) and (2), and their mixture, can be blended with other substances, primarily with other fragrances, to form novel fragrance compositions. In this connection, the proportion of the cyclododecenylacetonitrile, especially the mixture amounts generally up to 60% by weight, preferably 1-50% by weight of the fragrance composition. By virtue of the addition of cyclododecenylacetonitrile, the compositions gain a rounded aroma, without losing their interesting, characteristic fragrance note. It is surprising that, as illustrated in the examples which follow, this effect is obtained in compositions and perfume bases having widely differing fragrance characteristics.

Fragrance compositions containing cyclododecenylacetonitrile, especially mixture thereof, can serve as a perfume or for the perfuming of cosmetics, such as, for example, creams, toilet soaps and lotions. They can also be utilized to improve the scent of industrial products, such as, for example, detergents and cleaning agents, disinfectants and textile finishing agents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Synthesis of Cyclododecenylacetonitrile

An agitator-equipped apparatus provided with thermometer, reflux condenser, and water trap is charged with the following materials:

| 434 g (5 mol) | cyanoacetic acid |
|---|---|
| 910 g (5 mol) | cyclododecanone |
| 650 g | toluene |
| 21 g | ammonium acetate |

The reaction mixture is heated to boiling under reflux at 128°–130° C. for 30 hours with agitation and under nitrogen; the water formed (80 g) is collected in the water trap. Carbon dioxide is evolved during the course of the reaction.

The reaction mixture is distilled the rough a short glass column filled glass Raschig rings. First, a toluene is distilled off under atmospheric pressure. Then, the nitrile mixture, boiling range of 120°–180° C. at 18–20 mbar, is separated.

The nitrile distillate is fractionated on a 0.5 m glass column filled with multifill packing elements. At 13 mbar, 729 g of distillate is obtained boiling in the range 170°–179° C.

The purity of the nitrile mixture, which contained three components, determined by gas chromatography, is 99.1%. The amounts of individual components present were:

| 1st Component | 63.2% |
|---|---|
| 2nd Component | 32.0% |
| 3rd Component | 3.9% |

Components 1 and 2 correspond to structure (1) and are the cis and trans isomers. The third and minor component corresponds to structure (2). The overall yield of the three-component mixture was 71.1%.

The three component mixture has a pronounced ammonia odor. To remove that odor, about 50–200 liters of nitrogen per hour is passed through 1–5 liters of the mixture at ambient temperatures (15°–30° C.) or higher, up to about 100° C., by means of a pipe having a constricted end (tapered or provided with a porous plate at the end) immersed in the product. Depending on temperature, 0.5–5 hours is required; the end point of the gas feeding step is readily detected by the marked improvement in odor of the product.

A very pure mixture of isomers of cyclododecenylacetonitrile is obtained, having a pleasant scent reminiscent of rose and lily of the valley and additionally encompassing a musk note. This mixture, as well as its individual isomer, can be used as a fragrance or in the preparation of fragrance compositions.

EXAMPLE 2

A flowery "lily of the valley composition" is prepared by mixing the following components:

| 25 parts | jasmine base |
|---|---|
| 3 parts | phenylethyl isobutyrate |
| 5 parts | geraniol 98 = 2-trans-3,7-dimethyl-2,6-octadien-8-ol (commercial product of BBA) |
| 5 parts | citronellol = 3,7-dimethyl-6-octen-1-ol (commercial product of BBA) |
| 1 part | methyl cinnamate 1% |
| 10 parts | β-phenylethanol |
| 30 parts | "Lilial" = p-tert-butyl-α-methylphenylpropionaldehyde (commercial product of GIVAUDAN SA) |
| 5 parts | cyclamen aldehyde = p-isopropyl-α-methylphenylpropionaldehyde |
| 9 parts | linalool, synthetic = 3,7-dimethyl-1,6-octadien-3-ol (commercial product of GIVAUDAN SA) |
| 93 parts | total |

This composition has the typical lily of the valley scent.

The addition of 32 parts of cyclododecenylacetonitrile yields 125 parts of a novel fragrance composition exhibiting not only the flowery lily of the valley note but also a fuller, rounded scent spectrum with, in part, a more tart, spicy character.

EXAMPLE 3

A so-called VIOLETTE composition is produced by mixing the following components:

| 480 parts | "Vestinol" C = o-phthalic acid di-n-butyl ester (commercial product of CWH) |
|---|---|
| 25 parts | "Cedrol", see S. Arctander, Perfume and Flavor Chemicals Montclair N.J. (USA) .1969, No. 598 (commercial product of MANE FILS) |
| 20 parts | "Base Vert de Violette"(commercial product of E.R.P.) |
| 175 parts | "Colophane" (commercial product of D.R.T) |
| 50 parts | "Ionone Savon" (commercial product of SORDES) |
| 100 parts | "Terpens d'Isorone" (commercial product of SORDES) |
| 25 parts | benzyl benzoate |
| 50 parts | "Bois de Cédre de Virgine" (commercial product of ADRIEN) |
| 25 parts | benzyl acetate |
| 50 parts | "Terpinéol" (commercial product of D.R.T.) |
| 100 parts | total |

This composition has a woody, somewhat shallow fragrance reminiscent of tree rosins.

The addition of 50 parts of cyclododecenylacetonitrile results in 150 parts of a novel fragrance composition with a scent that is more rounded as compared with the above-described composition and contains a full, warm component.

EXAMPLE 4

A so-called "SANTAL" base composition is prepared by mixing the components set out below:

| 36 parts | isobornyl cyclohexanol |
|---|---|
| 29.8 parts | "Dicydol" = 3(4),8(9)-dihydroxymethyl-tricyclo[5.2.1$^{2,6}$]decane (commercial product of RUHRCHEMIE) |
| 9 parts | methylcyclododecyl ether (10% strength) |
| 3 parts | "Arova" = 1,4-dioxacyclohexadecane-5,16-dione CXBM (commercial product of E.R.P.) |
| 0.2 part | "Prunolide" (10% strength) (commercial product of GIVAUDAN) |
| 2 parts | formate of trans-β-decahydronaphthol |

-continued

| 80 parts total |

This composition has a sweetish, musk-like scent reminiscent of sandalwood.

The addition of 20 parts of cyclododecenylacetonitrile results in 100 parts of a novel fragrance base with a scent that is more rounded, warmer, milder as compared with the starting mixture and has a somewhat more flowery note.

EXAMPLE 5

A special, so-called PATCHOULY base composition is prepared by mixing the following components:

| | |
|---|---|
| 5 parts | isobornyl cyclohexanol |
| 5 parts | "Dicydol" (see Example 4) |
| 17 parts | methylcyclododecyl ether (10% strength) |
| 1 part | formate of trans-8-decahydronaphthol |
| 10 parts | formate of p-tert-butylcyclohexanol |
| 10 parts | "Vertofix coeur" (commercial product of IFF) |
| 1 part | p-tert-butylcyclohexanol |
| 5 parts | "Vetchouly" (commercial product of BERJE) |
| 20 parts | "Bomme Copahn" (commercial product of ADRIEN) |
| 10 parts | "Bomme Gurjum" (of the same firm) |
| 5 parts | "Acetat des Cédrényle", S. Arctander, Perfume and Flavor Chemicals Montclair N.J. (USA), 1969, No. 597 (commercial product of IFF) |
| 1 part | isocyclocitral, S. Arctander, Perfume and Flavor Chemicals Montclair N.J. (USA), 1969, No. 761 (commercial product of the same firm) |
| 2 parts | "Perou Bomme" (commercial product of ADRIEN) |
| 0.25 part | "Mélange PM 531/PM 517 à 2%" (pyrazines) (commercial product of BBA) |
| 3 parts | formaldehyde dicyclododecylacetal |
| 2.75 parts | cyclododecenone |
| 98 parts total | |

This composition has the characteristic patchouly aroma.

The addition of 27 parts of cyclododecenylacetonitrile results in 125 parts of a novel (fragrance) base wherein the patchouly flavor is retained, but which exhibits a rounded scent with a warm, refreshing note.

What is claimed is:

1. A fragrance composition comprising a flavor-imparting amount of cyclododecenylacetonitrile and at least one other fragrance component.

2. A fragrance composition according to claim 1, comprising up to 60% by weight of cyclododecenylacetonitrile.

3. A composition according to claim 1, comprising 1-50% by weight of cyclododecenylacetonitrile.

4. A method of imparting a more rounded scent to a fragrance composition, comprising adding to said fragrance composition a flavor-imparting amount of cyclododecenylacetonitrile.

5. A method according to claim 4, wherein said fragrance composition has a Lilly of the Valley scent and the addition of said cyclododecenylacetonitrile imparts a fuller rounded scent spectrum with a more tart, spicy character.

6. A method according to claim 4, wherein said fragrance composition has a woody, somewhat shallow fragrance reminiscent of of tree rosins, and the addition of cyclododecenylacetonitrile results in a more rounded scent with a full, warm component.

7. A method according to claim 4, wherein said fragrance composition has a sweetish, musk-like scent reminiscent of sandlewood, and the addition of said cyclododecenylacetonitrile results in a more rounded, warmer, milder composition as compared to the starting mixture, and has a somewhat more flowery note.

8. A method according to claim 4, wherein the fragrance composition has a patchouly aroma and the addition of said cyclododecenylacetonitrile imparts a rounded scent with a warm, refreshing note.

9. A method according to claim 4 wherein not more than 60% by weight of cyclododecenylacetonitrile is added.

10. A method according to claim 4 wherein 1-50% by weight of cyclododecenylacetonitrile is added.

* * * * *